United States Patent
Chen et al.

(10) Patent No.: US 9,089,303 B2
(45) Date of Patent: Jul. 28, 2015

(54) AUTOMATED ASSESSMENT OF SKIN LESIONS USING IMAGE LIBRARY

(71) Applicant: LUBAX, INC., Pasadena, CA (US)

(72) Inventors: Raymond H. Chen, San Marino, CA (US); Ramez Emile Necola Shehada, La Mirada, CA (US)

(73) Assignee: LUBAX, INC., Pasadena, CA (US)

( * ) Notice: Subject to any disclaimer, the term of this patent is extended or adjusted under 35 U.S.C. 154(b) by 0 days.

(21) Appl. No.: 13/674,848

(22) Filed: Nov. 12, 2012

(65) Prior Publication Data

US 2013/0218026 A1 Aug. 22, 2013

Related U.S. Application Data

(63) Continuation of application No. 12/475,412, filed on May 29, 2009, now Pat. No. 8,330,807.

(51) Int. Cl.
| | |
|---|---|
| H04N 9/47 | (2006.01) |
| A61B 5/00 | (2006.01) |
| G06F 19/00 | (2011.01) |
| G06K 9/00 | (2006.01) |
| G06T 7/00 | (2006.01) |

(52) U.S. Cl.
CPC ............ *A61B 5/444* (2013.01); *A61B 5/0059* (2013.01); *A61B 5/0077* (2013.01); *A61B 5/445* (2013.01); *A61B 5/7246* (2013.01); *A61B 5/7264* (2013.01); *A61B 5/7282* (2013.01); *A61B 5/7475* (2013.01); *G06F 19/321* (2013.01); *G06F 19/3443* (2013.01); *G06K 9/00* (2013.01); *G06T 7/0014* (2013.01); *G06K 2209/05* (2013.01); *G06K 2209/053* (2013.01); *G06T 2207/30088* (2013.01)

(58) Field of Classification Search
USPC ................................................ 348/61, 73, 77
See application file for complete search history.

(56) References Cited

U.S. PATENT DOCUMENTS

| | | | |
|---|---|---|---|
| 5,437,278 A | 8/1995 | Wilk | |
| 5,807,256 A * | 9/1998 | Taguchi et al. | ............... 600/425 |
| 6,415,295 B1 * | 7/2002 | Feinberg | ............................... 1/1 |
| 6,925,199 B2 | 8/2005 | Murao | |

(Continued)

OTHER PUBLICATIONS

US Patent and Trademark Office. 2015. Office Action, dated Jan. 8, 2015, for U.S. Appl. No. 13/892,184, Chen, Raymond H. et al., entitled "Automated Assessment of Skin Lesions Using Image Library," filed May 10, 2013, and published Sep. 26, 2013, as U.S. Publication No. 20130253337.

(Continued)

*Primary Examiner* — Joshua Joo
(74) *Attorney, Agent, or Firm* — McDermott Will & Emery LLP (57) ABSTRACT

An automated skin lesion assessment system may automatically assess a suspect skin lesion. An electronic image library may contain diagnosed skin lesion image data representative of images of a plurality of diagnosed skin lesions and, for each, a diagnosis of the skin lesion. An image capture system may capture an image of the suspect skin lesion. A computer processing system may compare the image of the suspect skin lesion with the diagnosed skin lesion image data and, based on this comparison, identify one or more diagnosed skin lesions which match the suspect skin lesion. A user interface may report the diagnoses of the diagnosed skin lesions that match the image of the suspect skin lesion.

9 Claims, 3 Drawing Sheets

(56) References Cited

U.S. PATENT DOCUMENTS

| | | | |
|---|---|---|---|
| 6,993,167 B1 | 1/2006 | Skladnev et al. | |
| 7,233,693 B2 * | 6/2007 | Momma | 382/162 |
| 7,738,032 B2 | 6/2010 | Kollias et al. | |
| 7,894,651 B2 * | 2/2011 | Gutkowicz-Krusin et al. | 382/128 |
| 8,026,942 B2 | 9/2011 | Payonk et al. | |
| 8,094,186 B2 * | 1/2012 | Fukuoka et al. | 600/306 |
| 8,109,875 B2 * | 2/2012 | Gizewski | 600/306 |
| 8,330,807 B2 | 12/2012 | Chen et al. | |
| 2002/0021828 A1 | 2/2002 | Papier et al. | |
| 2005/0049509 A1 | 3/2005 | Mansour et al. | |
| 2005/0171974 A1 * | 8/2005 | Doering | 707/104.1 |
| 2006/0089570 A1 | 4/2006 | Mansour et al. | |
| 2008/0009707 A1 * | 1/2008 | Theriault | 600/410 |
| 2008/0037876 A1 * | 2/2008 | Galperin | 382/203 |
| 2008/0215525 A1 | 9/2008 | Kakimoto et al. | |
| 2008/0243395 A1 | 10/2008 | Oosawa et al. | |
| 2008/0262327 A1 | 10/2008 | Kato | |
| 2008/0275315 A1 | 11/2008 | Oka et al. | |
| 2009/0060304 A1 | 3/2009 | Gulfo et al. | |
| 2009/0196475 A1 | 8/2009 | Demirli et al. | |
| 2009/0245603 A1 * | 10/2009 | Koruga et al. | 382/128 |
| 2010/0279718 A1 * | 11/2010 | Borve | 455/466 |
| 2013/0253337 A1 | 9/2013 | Chen et al. | |

OTHER PUBLICATIONS

US Patent and Trademark Office. 2014. Office Action, dated May 8, 2014, for U.S. Appl. No. 13/892,184, Chen, Raymond H. et al., entitled "Automated Assessment of Skin Lesions Using Image Library," published Sep. 26, 2013, as U.S. Publication No. 20130253337.

* cited by examiner

AUTOMATED ASSESSMENT OF SKIN LESIONS USING IMAGE LIBRARY

CROSS-REFERENCE TO RELATED APPLICATION

This application is a continuation application of U.S. patent application Ser. No. 12/475,412, entitled "Automated Assessment of Skin Lesions Using Image Library" filed May 29, 2009, now U.S. Pat. No. 8,330,807, issued Dec. 11, 2012, the entire content of which is incorporated herein by reference.

BACKGROUND

1. Technical Field

This disclosure relates to the assessment of skin lesions.

2. Description of Related Art

Some patients are hesitant to seek the advice of a physician about a skin lesion. These patients may not believe that the skin lesion is of sufficient importance to warrant the cost and/or inconvenience of visiting a physician, or the potential embarrassment of the examination. Sometimes, these decisions not to seek medical advice can result in a harmful skin lesion not being diagnosed in a timely manner.

Automated devices have been created which provide a patient with an automated assessment of a skin lesion, without the need for an examination by a physician. Such devices use image-recognition techniques to identify features in the lesions which may or may not be indicative of a problem. Unfortunately, these assessments may not be accurate and the algorithms which these devices employ may be difficult to update with later-discovered improvements in analytical approaches which are taken.

SUMMARY

An automated skin lesion assessment system may automatically assess a suspect skin lesion. An electronic image library may contain diagnosed skin lesion image data representative of images of a plurality of diagnosed skin lesions and, for each, a diagnosis of the skin lesion. An image capture system may capture an image of the suspect skin lesion. A computer processing system may compare the image of the suspect skin lesion with the diagnosed skin lesion image data and, based on this comparison, identify one or more diagnosed skin lesions which match the suspect skin lesion. A user interface may report the diagnoses of the diagnosed skin lesions that match the image of the suspect skin lesion.

The computer processing system may determine that a diagnosed skin lesion matches the suspect skin lesion by determining that the diagnosed skin lesion has a threshold level of similarity to the suspect skin lesion.

The computer processing system may determine that a diagnosed skin lesion matches the suspect skin lesion by comparing a plurality of features of the skin lesions. The compared features may include at least two or four of the following: size, color, degree of color uniformity, shape, edge smoothness, and location. The computer processing system may determine that a diagnosed skin lesion matches the suspect skin lesion by giving a different weight to similarities between at least two of the features.

The user interface may report only a single diagnosis. The user interface may report the most frequent diagnosis among the matches made by the computer processing system or the diagnosis of the diagnosed skin lesion which most closely matches the suspect skin lesion.

The user interface may report a plurality of diagnoses, such as the diagnoses of the diagnosed skin lesions which match the suspect skin lesion.

The user interface may report information indicative of the quantity of matching diagnosed skin lesions which had each reported diagnosis. The quantity may be reported as a percentage of all of the matching diagnosed skin lesions.

The image capture system may include a camera configured to capture the image of the suspect skin lesion, a lens configured to focus an image of the skin lesion on the camera, a housing containing the camera and the lens and configured to block external light from illuminating the suspect legion while the camera captures the image of the suspect skin lesion, and an illumination system within the housing and configured to illuminate the suspect skin lesion while the camera captures the image of the suspect skin lesion.

The housing may be configured to insure that the lens of the camera is a fixed distance from the skin lesion when the skin lesion is placed against a front opening of the housing.

The housing may have a cone-like shape.

A handle may be attached to the housing. An electronic switch may be in the handle and, when activated, cause the image of the suspect skin lesion to be captured.

A protective annulus may be detachably connected to a front opening of the housing so as to prevent the housing from coming in contact with the suspect skin lesion.

The illumination system may include one or more LEDs. The LEDs may emit white light or a monochromatic light.

The illumination system may be positioned behind the lens.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it is intended to refer to the same or like components or steps.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Two types of systems will now be described. The first system may be used to capture images of skin lesions which have been diagnosed and the diagnoses of them. The second system may provide an analysis of a suspect skin lesion based on a comparison of the suspect skin lesion with this captured data.

Figure 1:
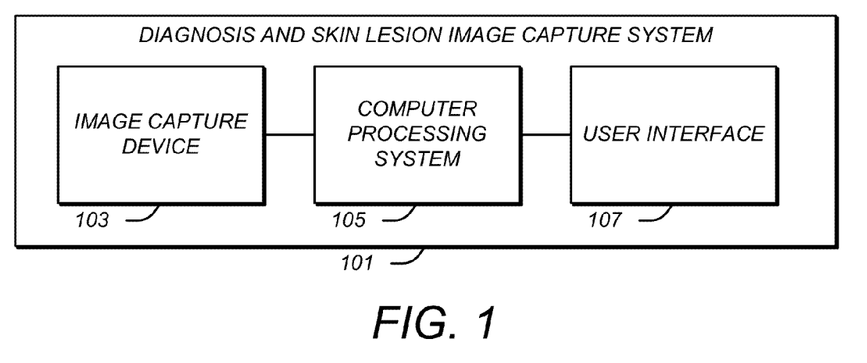
FIG. 1 is a block diagram of a system which captures skin lesion images and diagnoses of them.

FIG. 1 is a block diagram of a system which captures skin lesion images and diagnoses of them.

As illustrated in FIG. 1, a diagnosis and skin lesion image capture system 101 may include an image capture device 103, a computer processing system 105, and a user interface 107.

The image capture device 103 may be configured to capture an image of the suspect skin lesion. The image capture device 103 may be configured to ensure consistency and uniformity among the images which are captured. For example, the image capture device 103 may be configured to ensure that the intensity and spectral distribution of the light which illuminates each skin lesion when its image is being captured is always substantially the same. Similarly, the image capture device 103 may be configured to ensure that differences in the size of skin lesions in the images are representative of actual differences in the size of the skin lesions, not merely changes in image scale.

Figure 2:
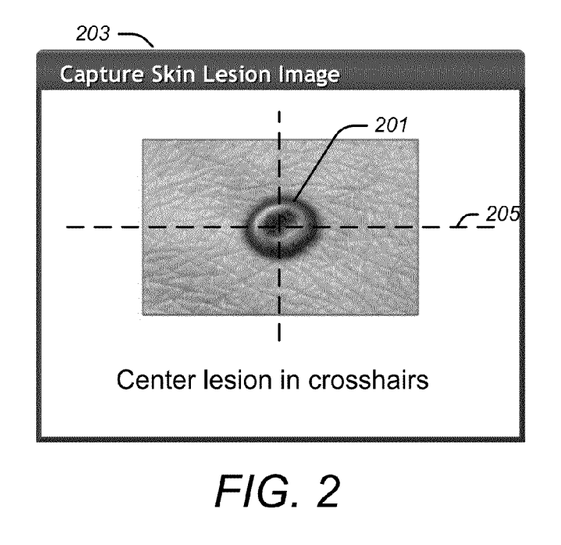
FIG. 2 illustrates a computer display window which displays a skin lesion being captured by a skin lesion image capture device.

Any type of image capture device may be used for the image capture device 103. One example of such a device is illustrated in FIG. 2 and is discussed below.

The user interface 107 may be configured to interface with a physician or other user of the diagnostic and skin lesion image capture system 101. The user interface 107 may be configured to allow the user to enter information about the patient whose skin lesion is being imaged, such as the name of the patient, the patient's date of birth, and the patient's address. The user interface 107 may be configured to allow information about the lesion to be entered, such as the general location of the lesion on the patient's body.

The user interface 107 may be configured to allow the user, such as a physician, to enter a diagnosis of the skin lesion. To facilitate this, the user interface 107 may be configured to provide a list of possible diagnoses and to require the user to select the most appropriate one. In the event of uncertainty about the diagnosis, the user interface 107 may be configured to allow the user to enter more than a single diagnosis.

The user interface 107 may be configured to allow the user to select one or more of the diagnoses by utilizing a hierarchical menu. The user interface 107 may in addition or instead be configured to allow the user to enter a diagnosis without selecting it from a list, such as by typing it in or by stating it verbally.

The user interface 107 may be configured to assist the user during the process of capturing an image of the skin lesion. For example, the user interface 107 may include a display which displays the image of the skin lesion which is being captured by the image capture device 103 in real time. This may enable the user to verify that the image is being faithfully captured. It may also enable the user to adjust the image capture device 103 so as to cause the image of the skin lesion to be positioned at the center of its capture frame.

FIG. 2 illustrates a computer display window which displays a skin lesion being captured by a skin lesion image capture system. As illustrated in FIG. 2, the display may depict a skin lesion 201 which is being captured by the image capture device 103 within a window 203. The window 203 may include crosshairs 205 positioned at approximately at the center of the image capture frame. The user may adjust the position of the image capture device 103 while viewing the image which it is capturing in the window 203 until such time as the skin lesion 201 appears to be centered within the crosshairs 205, as illustrated in FIG. 2. The user interface 107 may in addition or instead provide other forms of communication that may assist the user in adjusting the position of the image capture device 103.

The user interface 107 may be configured to display information about the skin lesion which is being captured, such as information about its size. The user interface 107 may be configured to display other information, such as the patient's name, date of birth, the location of the skin lesion, and/or the diagnosis which a physician has provided about the skin lesion.

The user interface 107 may include any type of user interface device. For example, the user interface 107 may include one or more displays, touch screens, keyboards, mice, sound systems, and/or printers. When a printer is provided, the user interface 107 may be configured to print some or all of the information which it displays, as well as additional information that may be of interest. For example, the user interface 107 may be configured to print an image of the skin lesion which the physician may place in the patient's medical file. The printed image may be marked with patient-identifying information, the physician's diagnosis, size information about the lesion, and/or with any other information.

The computer processing system 105 may be configured to cause the diagnosis and skin lesion image capture system 101 to perform each of the functions which have been described herein in cooperation with the image capture device 103 and/or the user interface 107.

The computer processing system 105 may be configured to cause the diagnosis and skin lesion image capture system 101 to perform other functions. For example, the computer processing system 105 may be configured to process image data from the image capture device 103 to correct for any spatial distortion in the image data which is delivered. For example, the image capture device 103 may use a wide-angle lens which may introduce barrel distortion caused by uneven magnification between the edges and center of the lens. Horizontal and vertical lines may appear to be bent outwards toward the edges of the image. The computer processing system 105 may be configured to apply algorithms to correct for this barrel distortion, such as algorithms of the type described in Mundhenk, T. N., et al., "Techniques for fisheye lens calibration using a minimal number of measurements," Proceedings of the SPIE, SPIE-Int. Soc. Opt. Eng., 4197, pp. 181-90, 2000, and e.g. James P. Helferty, et al., "Videoendoscopic Distortion Correction and Its Application to Virtual Guidance of Endoscopy," IEEE Transactions on Medical Imaging, Vol. 20, No. 7, pp 605-617, 2001, the entire contents of both of which is incorporated herein by reference.

The computer processing system 105 may include any type of computer processing components. For example, the computer processing system 105 may include one or more processors, memory devices, operating systems, application programs, and/or other computer hardware and/or software.

The computer processing system 105 may be at the same location as the image capture device 103 and/or the user interface 107, or it may be at a location that is remote from one or both of them. For example, the computer processing system 105 may be at a website which is being hosted at a remote server. In such a configuration, the image capture device 103 and the user interface 107 may be configured to communicate with the computer processing system 105 over a computer network. For example, the image capture device 103 and the user interface 107 may be part of a remote client workstation which communicates with the computer processing system 105 at a remote website over the internet.

The computer processing system 105 may be configured with one or more memory devices, such as one or more hard disk, CD's, DVD's, and/or flash memories, that store image data that is received from the image capture device 103 and that diagnoses and other information received from the user interface 107.

The computer processing system 105 may in addition or instead be configured to deliver image data which is received from the image capture device 103, as well the diagnoses and other information which are received from the user interface 107, to a remote location. At such remote location, information received from the computer processing system may be stored in a database, along with similar types of information received from other diagnosis and skin lesion image capture systems, and/or from other sources. The computer processing system 105 may be configured to deliver this information by any means, such as by burning a CD and/or DVD which may be physically delivered to the remote location, and/or by transmitting the information through any means, such as through a wired and/or wireless network communication system, such as over the internet.

Figure 3:
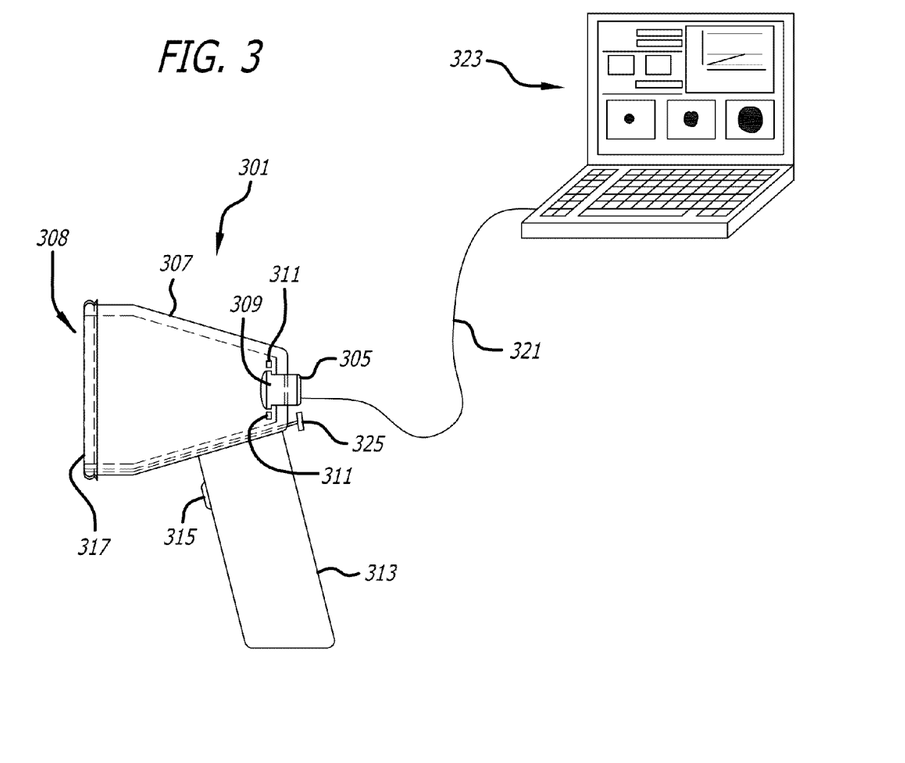
FIG. 3 is an example of a system which captures skin lesion images and diagnoses of them.

FIG. 3 is an example of a system which captures skin lesion images and diagnoses of them. As illustrated in FIG. 3, the system may include an image capture device 301 which may be connected to a laptop 323. The image capture device 301 may be configured to provide any one or more of the functions of the image capture device 103 that is illustrated in FIG. 1 and discussed above. Similarly, the laptop 323 may be configured to provide any one or more of the functions of the computer processing system 105 and the user interface 107 that are illustrated in FIG. 1 and discussed above. The diagnosis and skin lesion image capture system 101 in FIG. 1 may also be implemented with different components.

The image capture device 301 may include a camera 305, a housing 307 having a front opening 308, a lens 309, an illumination system 311, a handle 313, an electronic switch 315, and a protective annulus 317.

The camera 305 may be of any type. The camera 305 may an electronic camera and configured to capture a clear, high resolution, color, electronic image or a skin lesion. For example, the camera 305 may be a CCD camera having at least 3 megapixels. The camera 305 may be small and light.

As illustrated in FIG. 3, the camera 305 may be mounted at the rear of the housing 307. The distance between the camera 305 and the front opening 308 of the housing 307 may be too short to allow the camera 305 to focus on an accurate image of a skin lesion that is placed up against the front opening 308 of the housing 307. To assist the camera 306, the lens 309 may be placed in front of the camera 305. The lens 309 may be configured to focus the image of a lesion which is placed up against the front of the housing 307 on the camera 305. For example, the lens 309 may be a wide angle lens, such as a fisheye lens. The fisheye lens may have a wide field-of-view, such as a field-of-view between 140 and 160 degrees.

The housing 307 may be of any configuration and be made of any material. For example, the housing 307 may be made of an opaque material, such as an opaque plastic. The housing 307 may be configured to block external light from illuminating a skin lesion while the camera 305 captures an image of the skin lesion.

The housing 307 may be configured to ensure that the camera 305 is always the same distance from the front opening 308 of the housing 307. To facilitate this functionality, the housing 307 may be approximately in a cone-like shape, as illustrated in FIG. 3.

The front opening 308 of the housing 307 may have a diameter which is large enough to fully encompass the largest skin lesion which may be imaged. The front opening 308 may also have a diameter that is small enough so that all portions of the front opening 308 can come in contact with the patient's skin, even when the skin has some curvature, such as when the skin is covering a forearm. This may ensure that ambient light does not seep within the interior of the housing 307. For example, the front opening 308 may have a diameter of between ½ and 3 inches. The front opening 308 may instead be configured to have an adjustable diameter. Alternately, the front opening 308 may be configured to receive one of several different-sized adapters, so as to allow its diameter to be selected by the user.

The handle 313 may be attached to the housing 307, as illustrated in FIG. 3. It may be shaped and positioned so as to enable a user to easily place the front opening 308 of the housing 307 up against the skin of a patient and to easily adjust the precise position of the front opening 308 so that the skin lesion which is being imaged is positioned approximately within the center of the front opening 308, as illustrated in FIG. 2. During this positioning process, the camera 305 may be configured to continually capture images of the skin lesion and to deliver them to the laptop 323 over a cable 321, so that the user can see the effects of movements of the image capture device 301 in real time.

The electronic switch 315 may be positioned to be easily activated by one or more fingers of the user. The user may actuate the electronic switch 315 at such time as the image capture device 301 has been properly positioned over the skin lesion, such as when a display window of the type illustrated in FIG. 2 indicates that the skin lesion is positioned against and approximately within the center of the front opening 308. This may cause an image of the skin lesion to be permanently captured by the camera 305 and/or by the laptop 323.

The illumination system may be located within the housing 307 and may be configured to cast illuminating light on a skin lesion which is placed against and within the front opening 308. The illumination system 311 may be positioned behind the lens 309 of the camera 305, so as to prevent light from the illumination system from directly impinging upon the lens 309.

The illumination system 311 may be of any type. The illumination system 311 may be configured to provide illumination having an intensity and spectral distribution which remains constant throughout the use of the image capture device 301. For example, the illumination system 311 may include one or more LED's. One or more of these LED's may be of the miniature surface mount (SMD) type. The LED's may be configured to emit a white light, a monochrome light at a particular frequency, or light having any other type of spectral distribution. The intensity of the light from the illumination system 311 may be such as to fully illuminate a broad variety of skin lesions which are placed against and within the front opening 308, without saturating any portion of the images of these skin lesions which are captured by the camera 305.

In some embodiments, the intensity and/or spectral distribution of the illumination source 311 and/or the exposure of the camera 305 may be adjustable. These adjustments may be made manually by the user and/or automatically by the camera 305 and/or the computer processing system 105, based on the images which are captured by the camera 305. When adjustments are permitted, information about these adjustments may be automatically provided by or to the computer processing system 105 or manually entered through the user interface 107. Information about these adjustments may be delivered to the remote location for entry in the database, along with the other information about each captured image.

The protective annulus 317 may be configured as a bio isolator to protect the housing 307 from contact with the skin lesion or any other part of the patient. The protective annulus 317 may be made of any material and may be of any shape. For example, it may be made of a soft cushioning material, so as to aid in making a tight light seal and so as to feel comfortable to the patient. It may be circular.

Figure 4A:
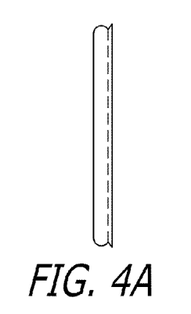
FIGS. 4(a)-4(c) illustrate a protective annulus that may be used with the skin lesion image capture system illustrated in FIG. 2.
Figure 4B:
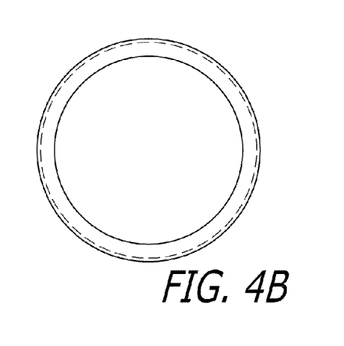
Figure 4C:
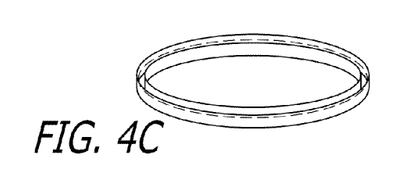

FIGS. 4(a)-4(c) illustrate a protective annulus that may be used with the skin lesion image capture system illustrated in FIG. 2. The protective annulus 317 illustrated in FIG. 3 may be of the type illustrate in FIGS. 4(a)-4(c) or of any other type.

As illustrated in FIG. 4, the protective annulus 317 may be configured to snap onto the front opening 308 of the housing 307. Thereafter, the protective annulus 317 may be configured to be released from the front opening 308 of the housing 307 through the actuation of an annulus release button 325. After use, the protective annulus 317 may be cleaned or discarded and replaced with a new one before the next use of the image capture device 301.

The image capture device 301 may communicate information to the laptop 323 through any means, such as through the cable 321 and/or through a wireless connection, such as a blue tooth connection. A USB cable connection may be provided which may also provide electrical power to the image capture device 301, including the camera 305 and/or the illumination source 311, A physician or other user may use the diagnosis and skin lesion image capture system 101, such as the embodiment illustrated in FIG. 3, to capture images of skin lesions on patients, as well as the diagnoses which the physician or other person has made of these skin lesions. To do so, the physician or other user may follow one or more of the capture procedures which have been discussed above, or any other procedure.

In one embodiment, all of the captured images may be captured under substantially identical lighting conditions. Thus, any differences in the color or texture of captured images may be solely attributable to actual color or texture differences. Similarly, all of the captured images may be captured with substantially the same zoom settings and distances between the skin lesions and the lens of the camera. Thus, any differences in the size of the lesions within each image may be solely attributable to actual sized differences.

Physicians and others may be induced to utilize the diagnosis and skin lesion image capture system 101 and/or others systems like it. Physicians and others may also be induced to provide the images and diagnoses which these systems capture to a remote location for entry in a common database. They may be induced to do so by the inclusion of a printer and/or other output device which may be configured to enable the physicians and other users to use the gathered information for the purpose of diagnosing their own patients. The diagnoses and skin lesion image capture system 101 may also be configured to enable the physician to recall such information during subsequent patient visits, thereby supplementing the information which the physician may have for future diagnoses.

Figure 5:
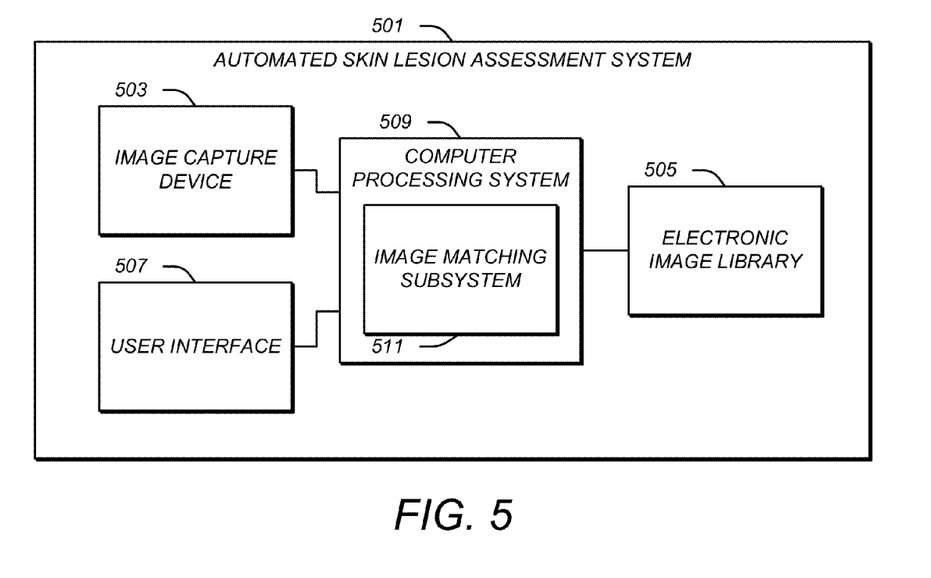
FIG. 5 is a block diagram of a system which automatically assesses a suspect skin lesion.

FIG. 5 is a block diagram of system which automatically assesses a suspect skin lesion. As illustrated in FIG. 5, an automated skin lesion assessment system 501 may include an image capture device 503, an electronic image library 505, a user interface 507, and a computer processing system 509 which may include an image matching subsystem 511.

The electronic image library 505 may be of any type. For example, the electronic image library may contain diagnosed skin lesion image data which is representative of images of a plurality of diagnosed skin lesions. The diagnosed skin lesion image data may include the diagnosis of each diagnosed skin lesion.

The diagnosed skin lesion image data which is contained within the electronic image library 505 may include images of various diagnosed skin lesions, all under substantially the same lighting conditions and all at substantially the same zoom levels and separation distances from the camera lens. If there is any variation among the lighting conditions, zoom levels, or separation distances, details about these variations may also be included.

The diagnosed skin lesion image data may include images of a wide variety of skin lesions, illustrative of a wide and comprehensive variety of skin lesion types and problems, including all of the most common skin lesion types and problems. For each diagnosis which is contained within the diagnosed skin lesion image data, there may be one, two, or several images of different diagnosed skin lesions with the same diagnosis.

The electronic image library 505 may include one or more electronic memories on which the diagnosed skin lesion image data may be recorded, such as one or more hard disk drives, CD's, DVD's, and/or flash drives. These memories may be in the same location as one or more of the other components of the automated skin lesion assessment system 501 and/or may be located remotely therefrom, in whole or in part. For example, the electronic image library 505 may be located at a centralized website which may be accessed by the other components of numerous automated skin lesion assessment systems of the type illustrated in FIG. 5. Through such centralization, updates to the electronic image library 505 may be readily made, without having to update each automated skin lesion assessment system 501 which may be in use. Alternatively, each automated skin lesion assessment system 501 may have its own electronic image library 505 and updates to this library may be provided through any means, such as through a computer network, such as the internet, and/or through CD's, DVD's, and/or flash memories.

The diagnosed skin lesion image data which is contained within the electronic image library 505 may come from any source. For example, it may come from diagnosis and skin lesion image capture systems of the type illustrated in FIG. 1 and discussed above.

The image capture device 503 may be configured to capture an image of a suspect skin lesion. The image capture device 503 may be any of the types of image capture devices that are discussed above in connection with the image capture device 103, such as the image capture device 301 illustrated in FIG. 3. The image capture device 503 may instead be of a different type. In either event, the image capture device 503 may be configured to generate images of a suspect skin lesion under the same illumination conditions, zoom level, and camera separation distance as was the diagnosed skin lesion image data in the electronic image library. In an alternate embodiment, the illumination, zoom level, and/or separation distance may be different, in which case information about these differences may be taken into consideration during the matching process described below.

The user interface 507 may be configured to assist the user in capturing an image of the suspect skin lesion while using the image capture device 503. It may be configured to do so in the same way as is discussed above in connection with the user interface 107. For example, the user interface 507 may be configured to display a window displaying the captured image of a suspect lesion while the user adjusts the position of the image capture device 503 to bring the suspect skin lesion within the center of its field of view, just like what is illustrated in FIG. 2 and discussed above. The user interface 507 may be configured to receive information from the user, such as information about the identity of the user, the location of the suspect skin lesion, and/or any type of information.

Unlike the user interface 107, however, the user interface 507 may not be configured to receive any diagnosis of the suspect skin lesion. In certain embodiments, the user interface 507 may also not be configured to receive any information identifying the patient.

The user interface 507 may be configured to report the diagnoses of the diagnosed skin lesions that match the image of the suspect skin lesion. Information about these matches may come from the computer processing system 509 as is described below in more detail. This report may be provided in any form. For example, the report may be provided on a display, in a printout, over a sound system, or in an e-mail.

The content of such a report may vary. In one embodiment, the report may provide only a single diagnosis. In this embodiment, the single diagnosis may be the most frequent diagnosis among the matches made by the computer processing system 509. In another embodiment, the single diagnosis may be the diagnosis of the diagnosed skin lesion which best matches the suspect skin lesion.

In another embodiment, the report may provide a plurality of diagnoses. In one embodiment, the diagnoses may be the diagnoses of all of the diagnosed skin lesions which match the suspect skin lesion. The report which may include information indicative of the quantity of matching diagnosed skin lesions which had each reported diagnosis. This quantity may be reported as a percentage of all of the matching diagnosed skin lesions.

Figure 6:
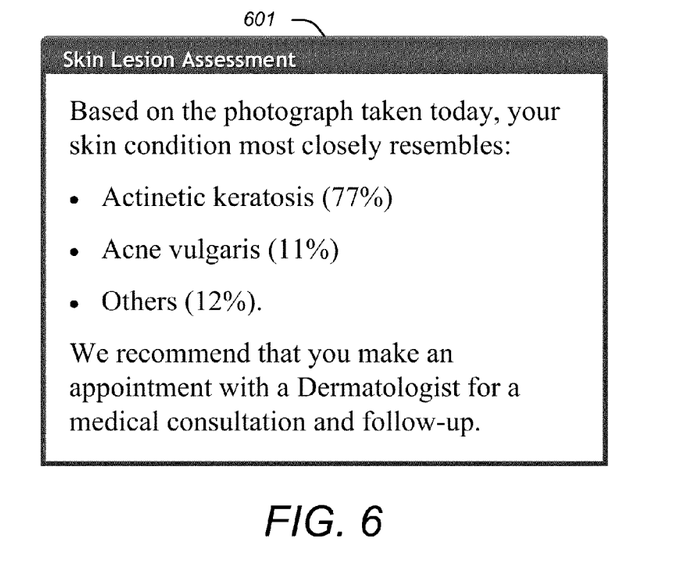
FIG. 6 illustrates a computer display window which displays an automated assessment of a suspect skin lesion.

FIG. 6 illustrates a computer display window which displays an automated assessment of a suspect skin lesion. As illustrated in FIG. 6, the user interface 507 may display a skin lesion assessment window 601 which may report all of the diagnoses that were made for the diagnosed skin lesions which match the suspect skin lesion. As reflected in FIG. 6, each reported diagnosis may include the percentage of matching diagnosed skin lesions which had that diagnosis.

The user interface 507 may be configured to provide other information to a user, such as information explaining the results which have been reported and urging the user to seek professional care, as also illustrated in FIG. 6. The user interface 507 may be configured to provide referrals to dermatologists that may be near the user. A dermatologist may, in turn, pay a fee to be given such referrals.

The user interface 507 may include one, some, or all of the components which are discussed above in connection with the user interface 107. For example, the user interface 507 may include one or more displays, keyboards, mice, touch screens, sound systems, printers, and/or any other type of user interface device.

The computer processing system 509 may be of any type. For example, the computer processing system 105 may include one or more processors, memory devices, operating systems, application programs, as well as any of the other components discussed above in connection with the computer processing system 105.

The computer processing system 509 may be configured to cause the automated skin lesion assessment system 501 to perform each of the functions which have been described herein in cooperation with the image capture device 503, the electronic image library 505, and/or the user interface 507. For example, the computer processing system 509 may be configured to compare the image of the suspect skin lesion which is generated by the image capture device 503 with the diagnosed skin lesion image data which is contained within the electronic image library 505. Based on this comparison, the computer processing system 509 may be configured to identify one or more diagnosed skin lesions which match the suspect skin lesion.

The computer processing system 509 may include an image matching subsystem 511. The image matching subsystem 511 may assist the computer processing system 509 in identifying these matches.

The image matching subsystem 511 may be configured to identify these matches using any approach. For example, the image matching subsystem 511 may be configured to determine that a diagnosed skin lesion matches the suspect skin lesion by determining that the diagnosed skin lesion has a threshold level of similarity to the suspect skin lesion.

The image matching subsystem 511 may be configured to compare a plurality of features of the suspect skin lesion with the diagnosed skin lesions. The image matching subsystem 511 may be configured to determine that a diagnosed skin lesion matches the suspect skin lesion by determining that one or more of these features of the diagnosed skin lesion has a threshold level of similarity to the suspect skin lesion. The features which may be compared may include size, color, degree of color uniformity, shape, edge smoothness, and/or the location of the lesion. In some configurations, two or more of these features may be compared. In other configurations, four or more of these features may be compared. Other features may be compared in addition or instead.

In some cases, the diagnosed skin lesions and the suspect skin lesion will have been imaged under the same lighting conditions and at the zoom level and camera separating distance. In other applications, they may have been captured under different lighting conditions, zoom levels, and/or separation distances. When there are differences, one or more of these image capture parameters may be noted within the diagnosed skin lesion image data that is contained within the electronic image library 505 and accounted for by the image matching subsystem 511 during the matching process.

The image matching subsystem 511 may generate a score indicative of the degree to which each compared feature matches. The determination by the image matching subsystem 511 as to whether there is a match may be based upon an analysis of these scores for each potential match which is examined. In some embodiments, similarities between some compared features may be given more weight in the analysis than between other compared features.

The image matching subsystem 511 may be configured to select the diagnosed skin lesion which best matches the suspect skin lesion. In alternate embodiments, the image matching subsystem 511 may be configured to select all diagnosed skin lesions which match the suspect skin lesion within a certain pre-determined range.

The image matching subsystem 511 may employ any type of image processing technique to facilitate this matching. For example, blob analysis algorithms may be utilized to analyze the area of each skin lesion. Once these regions are identified, the image matching subsystem 511 may calculate selected features of these regions, automatically discarding regions that are not of interest, and may classify remaining regions according to the values of the features. For example, a blob region may be identified by segmenting the image such that the pixels of an object have the same logical state. Regions of touching pixels in this state may be identified as a blob. Pixels not part of a blob may be considered as image background. The segmentation may include intensity thresholding, color thresholding, active contours, region growing and/or level set analysis. Further information about such techniques may be found in Pratt, William K., Digital Image Processing, John Wiley & Sons, New York, 2001, and e.g., Jahne, Bernd, Image Processing for Scientific Applications, CRC Press, New York, 1997, the entire contents of which are incorporated herein by reference.

The image matching subsystem 511 may include appropriate image processing software. For example, image processing software that is used in facial recognition may be adjusted to implement one or more of the approaches which have been described herein.

Like the electronic image library, the computer processing system 509 may be at the same location as the image capture device 503 and the user interface 507, or may be located remotely. For example, the computer processing system 509 may be at a remote website which is accessed by the image capture device 503 and/or the user interface 507 through a client station which is connected to the internet.

The components, steps, features, objects, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim embraces the corresponding acts that have been described and their equivalents. The absence of these phrases means that the claim is not intended to and should not be interpreted to be limited to any of the corresponding structures, materials, or acts or to their equivalents.

Nothing that has been stated or illustrated is intended or should be interpreted to cause a dedication of any component, step, feature, object, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

The invention claimed is:

1. An automated skin lesion assessment system for automatically assessing a suspect skin lesion comprising:
    an image library containing images of diagnosed skin lesions and, for each image of a diagnosed skin lesion, a diagnosis of the skin lesion;
    an image capture system that captures an image of the suspect skin lesion;
    a computer processing system that compares the image of the suspect skin lesion with the images of the diagnosed skin lesions and identifies the images of the diagnosed skin lesions that substantially match the image of the suspect skin lesion, at least two of the substantially matching images of the diagnosed skin lesions having different diagnoses; and
    a user interface that reports more than one of the diagnoses of the substantially-matching diagnosed skin lesions, together with information indicative of the quantity of the substantially-matching diagnosed skin lesions that had each reported diagnosis,
    wherein the information indicative of the quantity of the substantially-matching diagnosed skin lesions that had each reported diagnosis includes a relative number of substantially-matching diagnosed skin lesions that had each reported diagnosis in comparison to a total number of substantially-matching diagnosed skin lesions.

2. The automated skin lesion assessment system of claim 1 wherein the relative number of substantially-matching diagnosed skin lesions that had each reported diagnosis in comparison to the total number of substantially-matching diagnosed skin lesions includes a percentage of the substantially-matching diagnosed skin lesions that had each reported diagnosis in comparison to the total number of the substantially-matching diagnosed skin lesions.

3. The automated skin lesion assessment system of claim 1 wherein the information indicative of the quantity of the substantially-matching diagnosed skin lesions that had each reported diagnosis includes a listing of the diagnoses in descending order of the number of the substantially-matching diagnosed skin lesions that had each reported diagnosis.

4. An automated skin lesion assessment system for automatically assessing a suspect skin lesion captured by an image capture device comprising:
    an image library containing images of diagnosed skin lesions and, for each image of a diagnosed skin lesion, a diagnosis of the skin lesion;
    a computer processing system that:
    compares the image of the suspect skin lesion with the images of the diagnosed skin lesions and identifies the images of the diagnosed skin lesions that substantially match the image of the suspect skin lesion, at least two of the substantially matching images of the diagnosed skin lesions having different diagnoses; and
    communicates more than one of the diagnoses of the substantially-matching diagnosed skin lesions, together with information indicative of the quantity of the substantially-matching diagnosed skin lesions that had each communicated diagnosis,
    wherein the information indicative of the quantity of the substantially-matching diagnosed skin lesions that had each communicated diagnosis includes a relative number of substantially-matching diagnosed skin lesions that had each communicated diagnosis in comparison to a total number of substantially-matching diagnosed skin lesions.

5. The automated skin lesion assessment system of claim 4 wherein the relative number of substantially-matching diagnosed skin lesions that had each communicated diagnosis in comparison to the total number of substantially-matching diagnosed skin lesions includes a percentage of the substantially-matching diagnosed skin lesions that had each communicated diagnosis in comparison to the total number of the substantially-matching diagnosed skin lesions.

6. The automated skin lesion assessment system of claim 4 wherein the information indicative of the quantity of the substantially-matching diagnosed skin lesions that had each communicated diagnosis includes a listing of the diagnoses in descending order of the number of the substantially-matching diagnosed skin lesions that had each communicated diagnosis.

7. An automated skin lesion assessment system for automatically assessing a suspect skin lesion based on an image library containing images of diagnosed skin lesions and, for each image of a diagnosed skin lesion, a diagnosis of the skin lesion, the system comprising:
- an image capture system that captures an image of the suspect skin lesion;
- a computer processing system that requests a comparison of the image of the suspect skin lesion with the images of the diagnosed skin lesions and an identification of the images of the diagnosed skin lesions that substantially match the image of the suspect skin lesion, at least two of the substantially matching images of the diagnosed skin lesions having different diagnoses; and
- a user interface that reports more than one of the diagnoses of the substantially-matching diagnosed skin lesions, together with information indicative of the quantity of the substantially-matching diagnosed skin lesions that had each reported diagnosis, wherein the information indicative of the quantity of the substantially-matching diagnosed skin lesions that had each reported diagnosis includes a relative number of substantially-matching diagnosed skin lesions that had each reported diagnosis in comparison to a total number of substantially-matching diagnosed skin lesions.

8. The automated skin lesion assessment system of claim 7 wherein the relative number of substantially-matching diagnosed skin lesions that had each reported diagnosis in comparison to the total number of substantially-matching diagnosed skin lesions includes a percentage of the substantially-matching diagnosed skin lesions that had each reported diagnosis in comparison to a total number of the substantially-matching diagnosed skin lesions.

9. The automated skin lesion assessment system of claim 7 wherein the information indicative of the quantity of the substantially-matching diagnosed skin lesions that had each reported diagnosis includes a listing of the diagnoses in descending order of the number of the substantially-matching diagnosed skin lesions that had each reported diagnosis.

* * * * *